United States Patent
Imae et al.

(10) Patent No.: US 9,206,322 B2
(45) Date of Patent: Dec. 8, 2015

(54) NON-FLUORINATED COATING MATERIALS WITH ANTI-FINGERPRINT PROPERTY, AND EVALUATION METHOD THEREOF

(71) Applicant: National Taiwan University of Science and Technology, Taipei (TW)

(72) Inventors: Toyoko Imae, Taipei (TW); Ampornphan Siriviriyanun, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 244 days.

(21) Appl. No.: 14/038,777

(22) Filed: Sep. 27, 2013

(65) Prior Publication Data

US 2015/0090026 A1    Apr. 2, 2015

(51) Int. Cl.
| | | |
|---|---|---|
| B05D 1/08 | (2006.01) |
| B05D 1/10 | (2006.01) |
| B05D 1/12 | (2006.01) |
| C09D 143/04 | (2006.01) |
| C09D 5/16 | (2006.01) |
| G01N 33/32 | (2006.01) |

(52) U.S. Cl.
CPC .............. *C09D 5/1662* (2013.01); *G01N 33/32* (2013.01)

(58) Field of Classification Search
CPC ...................................................... G01N 33/32
USPC ....................................................... 73/150 R
See application file for complete search history.

(56) References Cited

U.S. PATENT DOCUMENTS

| | | | |
|---|---|---|---|
| 2003/0139620 A1* | 7/2003 | Yamaguchi .......... | C08G 65/007 556/445 |
| 2009/0297868 A1 | 12/2009 | Ito et al. | |
| 2011/0268899 A1 | 11/2011 | Albert et al. | |
| 2013/0115441 A1* | 5/2013 | Bookbinder .......... | B32B 17/068 428/323 |
| 2013/0157008 A1 | 6/2013 | Aytug et al. | |

FOREIGN PATENT DOCUMENTS

| | | |
|---|---|---|
| EP | 1645681 | 4/2006 |
| TW | 201114715 | 5/2011 |
| TW | 201129701 | 9/2011 |
| TW | 201244924 | 11/2012 |
| TW | 201336682 | 9/2013 |
| WO | 2013116134 | 8/2013 |

OTHER PUBLICATIONS

Cao et al., "Super water- and oil-repellent surfaces on intrinsically hydrophilic and oleophilic porous silicon films," Langmuir, Jan. 17, 2008, pp. 1640-1643, vol. 24.

(Continued)

*Primary Examiner* — Lisa Caputo
*Assistant Examiner* — Jamel Williams
(74) *Attorney, Agent, or Firm* — Jianq Chyun IP Office (57) ABSTRACT

The present application relates to an anti-fingerprint coating material. a method for evaluating a surface property. More particularly, the present application relates to a non-fluorinated coating materials with anti-fingerprint property, as well as a method for manufacturing thereof, and evaluating an anti-fingerprint properties of the coating materials surface and non-fluorinated coating materials with anti-fingerprint property.

9 Claims, 4 Drawing Sheets

(56) References Cited

OTHER PUBLICATIONS

Bellenger et al., "Surface structuration (micro and/or nano) governed by the fluorinated tail lengths toward superoleophobic surfaces," Langmuir, Jan. 2012, pp. 186-192, vol. 28.

Jung and Bhushan, "Wetting behavior of water and oil droplets in three-phase interfaces for hydrophobicity/philicity and oleophobicity/philicity," Langmuir, Jul. 28, 2009, pp. 14165-14173, vol. 25, Issue 24.

Ramos et al., "Superoleophobic behavior induced by nanofeatures on oleophilic surfaces," Langmuir. Dec. 15, 2009, pp. 5141-5146, vol. 26, Issue 7.

Barry et al., "The role of polarity in the structure of silanes employed in surface modification," Silanes and Other Coupling Agents. 2009, pp. 51-64, vol. 5, Leiden.

Imae et al., "Formation of organized adsorption layer by amphiphilic dendrimers," Colloid and Surfaces A: Physicochemical and engineering Aspects, Dec. 15, 2000, pp. 225-234, vol. 175.

Imae and Torii, "In-situ investigation of molecular adsorption on Au surface by surface-enhanced infrared absorption spectroscopy," J. Phys. Chem. B. Sep. 13, 2000, pp. 9218-9224, vol. 104.

Nakaoka and Imae, "Poly(amido amine) dendrimer adsorption onto 3-mercaptopropionic acid self-assembled monolayer formed on Au surface-investigation by surface enhanced spectroscopy and surface Plasmon sensing," Transactions of the Materials Research Society of Japan, 2001, pp. 945-948, vol. 26, Issue 31.

Ito and Imae, "Self-assembled monolayer of carboxyl-terminated poly(amido amine) dendrimers," Journal of Nanoscience and Nanotechnology, Jun. 2006, pp. 1667-1672, vol. 6.

Onoshima and Imae, "Dendritic nano- and microhydrogels fabricated by triethoxysilyl focal dendrons," First published online Dec. 14, 2005, Soft Matter, 2006, pp. 141-148, vol. 2.

Mitamura et al., "Fabrication and self-assembly of hydrophobic gold nanorods," J. Phys Chem. B. Jul. 11, 2007, pp. 8891-8898, vol. 111.

Sever et al., "Preparation and characterization of thin film by plasma polymerization of glycidoxypropyltrimethoxysilane at different plasma powers and exposure times," Applied Surface Science, Jul. 30, 2009, pp. 8450-8457, vol. 255.

Campos et al., "Fluoroalkyl-functinalized silica particles: Synthesis, characterization, and wetting characteristics,", Publication Date (Web): Jul. 5, 2011, Langmuir, 2011, pp. 10206-10215, vol. 27.

Kobayashi et al., "Wettability and antifouling behavior on the surfaces of superhydrophilic polymer brushes," Publication Date (Web): Apr. 16, 2012, Langmuir, 2012, pp. 7212-7222, vol. 28.

Wu et al., "Quantitative test method for evaluation of anti-fingerprint property of coated surfaces," Applied Surface Science, Jan. 15, 2011, pp. 2965-2969, vol. 257.

"Office Action of Taiwan Counterpart Application," issued on Jun. 23, 2015, p1-p5, in which the listed references were cited.

* cited by examiner

NON-FLUORINATED COATING MATERIALS WITH ANTI-FINGERPRINT PROPERTY, AND EVALUATION METHOD THEREOF

BACKGROUND OF THE INVENTION

1. Field of the Invention

The present application relates to an anti-fingerprint coating material. More particularly, the present application relates to a non-fluorinated coating materials with anti-fingerprint property, as well as a method for manufacturing thereof, and evaluating anti-fingerprint properties of the coating material.

2. Description of Related Art

For the electronic products with touch screen displays, such as game consoles, smart phones and tablet computers, the touch screens are operated by the touch of a finger. However, the fingerprint problem on the touch screen surface is a serious concern, which is usually addressed by the usage of protective coating materials.

The protective coating materials used to keep the electronic products surface clean should have a property which resist to both water and oil, since the fingerprint problem is caused by the sweat and sebum transferred from the users fingers. To aim to the clear appearance of the electronic products, a variety of approaches to develop a protective coating material has been revealed through the prior arts.

It is suggested that there are two factors contribute to the hydrophobic and oleophobic properties on surfaces: chemical composition and topography (roughness). To address the hydrophobic and oleophobic properties, the commonly used method is to modify the surface by using perfluoroalkyl-based compounds to impart the hydrophobic and oleophobic properties on surfaces. Besides, silica particles existed in the surface modification composition have also been used to create roughness, making the surface hydrophobic. Separately, the colloidal silica nanoparticles with fluoroalkylsilane have been mounted on the glass surface to construct siloxane film with super repellency for liquids. In addition, hybrid films consisting of fluoropolymer and silica particles have been fabricated to generate strawberry-like or quincunx-shaped composite silica particles on glass surfaces for achieving hydrophobic properties.

Although fluorinated compounds are guaranteed as a most favorable chemical to assure anti-fingerprint property, the high cost and environment risks cannot be passed over. In order to avoid environmental pollution, a variety of coating materials have been taught in prior art.

U.S. Pat. No. 2008/0131706 discloses a polysilazane-based composition as a permanent anti-fingerprint coating. The composition contains no chromium; therefore environmental pollution problems are avoided. However, the organic resin is highly specific and therefore difficult to produce. In addition, the composition is only used for application to a metal surface.

U.S. Pat. No. 2006/0110537 discloses an anti-fingerprint coating construction which has anti-corrosion, anti-dust, and anti-fingerprint characteristics. When the coating construction is employed on a surface, sweat on users' fingers is not liable to be adhered to the surface. Besides, the coating construction contains no chromium and doesn't need to process by an acid or alkali solution. This makes the coating construction environmentally friendly. Although this coating construction is with great properties, this trail is aim to an eco-friendly coating material without causing heavy metal pollution.

It is an object of the present invention to provide an anti-fingerprint coating material which is halogen free. Furthermore, the anti-fingerprint coating of the present invention produced from a manufacture process without eco-risk conditions, such as UV-light or high temperature treatment.

In the context of the present invention, the anti-fingerprint coating material is fabricated through simple and popular self-assembly method. It is known that the driving force for the self-assembly is the in-situ formation of polysiloxane, which is connected to surface silanol group (—SiOH) via Si—O—Si bonds. The self-assembling molecules consist generally of three parts: the head group, the alkyl chain and the terminal end group. The head group, i.e., trichloro-, trimethoxy- or triethoxysilane, is responsible for the anchoring of the molecules onto the substrate. The alkyl chain provides the stability of the monolayer; the terminal end group introduces chemical functionality into the monolayer system. The head group of the self-assembling molecules form the Si—O—Si bond through nucleophilic substitution which can occur in organic compounds that have an electronegative atom or group bonded to a sp3 hybridized carbon. And since halogens are more electronegative than carbon, so they have a larger share of the electrons. This polar C-halogen bond causes the head group of the self-assembling molecules to undergo substitution reactions. Since the electronegativity of C-halogen facilities the SiOH surface binding, more precise control of the reaction conditions is needed for organosiliane SAM to make self molecular assemble.

High quality self-assembly monolayers (SAM) are not easy to acquire, because of the need to carefully control the amount of water in solution. As understood, incomplete monolayers are form in the absence of water, excess water results in facile polymerization in solution and polysiloxane deposition of the surface. Depending on the water content of the silane solution, two types of SAM growth behavior has been observed: homogeneous growth and island-type growth (Valiant et al.). As observation, the more water content existed in the SAM reaction environment, the more pre-organized aggregation of siloxanes is formed. The island-type growth SAM can make the coated surface bumpy, and expectedly the surface roughness can be adjusted by control the water content in the reaction environment.

Temperature has been found to play an important role in monolayer formation. Different temperatures can cause the different reactions of hydrolyzed reactive group (such as trichlorosilyl) with the other reactive group in solution or with the other reactive group in the Si—OH surface. Moreover, the influence of the other parameters such as solvent, solution age, terminal function group, alkyl chain length, surface Si—OH group concentration, deposition time are also reported (Wasserman et al., 1989; Silberzan et al., 1991; Grange at al., 1993; Rye, 1997; Sagiv, 2009).

Besides the anti-fingerprint coating materials, the applicant also finds that the traditional evaluating method for anti-fingerprint surface properties is not enough. Since the chemical constituent of human's fingerprint is mainly composed of water and oleic acid and its derivatives. Using water drop test to examine the hydrophobic surface property does not represent anti-fingerprint properties. Therefore, in the present application, a systemic method for evaluating surface properties of a surface of a glass substrate is provided.

SUMMARY OF THE INVENTION

The present application is directed to a coating material with anti-fingerprint property. Also, the application of the contact angle of oleic acid on a target surface for effectively evaluating the anti-fingerprint property of the target surface is provided.

In the present application, self-assembled monolayers (SAMs) of silane coupling reagents have been fabricated on the glass surface through sol-gel reaction to develop hydrophobic/oleophobic (solvophobic) properties with an aim of verifying the anti-fingerprint effect. The solvophobicity of the glass surface was characterized by contact angle measurement. The results indicated that a fabrication of siloxane SAMs on the glass revealed a significant change in solvophobicity of glass surface. According to embodiments of the present invention, the surface of the glass substrate may be modified with an organooxysilane compound before providing the glass substrate, so that the surface of the modified glass substrate becomes a modified surface.

According to embodiments of the present invention, the organooxysilane compound is trimethoxymethylsilane (TMS) or a hybrid of trimethoxymethylsilane (TMS) and octadecyltrimethoxysilane (ODS).

In the present application, a method for evaluating one or more surface properties of a surface of a glass substrate is provided. After providing the glass substrate having the surface, one or more water droplets are dropped to the surface. A first contact angle of water on the surface of the glass substrate is measured, and then the first contact angle is compared with a first reference angle to determine a first surface property of the surface. Also, one or more droplets of oleic acid are dropped onto the surface. A second contact angle of oleic acid on the surface of the glass substrate is measured and the second contact angle is compared with a second reference angle to determine a second surface property of the surface.

According to embodiments of the present invention, the first surface property is a hydrophilic/hydrophobic property and the first reference angle is 40 degrees. The second surface property is an anti-fingerprint property and the second reference angle is 40 degrees.

According to embodiments of the present invention, one or more n-hexadecane droplets are also dropped onto the surface. A third contact angle of n-hexadecane on the surface of the glass substrate is measured and the third contact angle is compared with a third reference angle to determine a third surface property of the surface.

According to embodiments of the present invention, the third surface property is an oleophilic/oleophobic property, and the third reference angle is 40 degrees.

In order to make the above and other features and advantages of the present invention more comprehensible, embodiments accompanied with figures are described in detail below.

BRIEF DESCRIPTION OF THE DRAWINGS

Common reference numerals are used throughout the drawings and the detailed description to indicate the same elements. The present invention will be more apparent from the following detailed description taken in conjunction with the accompanying drawings.

DESCRIPTION OF EMBODIMENTS

In the present application, the contact angle of oleic acid on a target surface is used for evaluating the anti-fingerprint property of the target surface. Conventionally, the anti-fingerprint property is considered related with hydrophobicity and/or oleophobicity. However, as noted by the Applicants, the anti-fingerprint property is not necessarily consistent with hydrophobicity from conventional organic solvents and thus the evaluation of the anti-fingerprint property using merely water or organic solvents may be inaccurate. Using the additional test liquid, oleic acid, the contact angles of oleic acid may be used to fortify the evaluation of the anti-fingerprint property of a target surface. Thus, the surface characteristics of the target surface(s) can be determined more precisely and accurately.

Also, such approach may be used to evaluate the hydrophobicity or anti-fingerprint character of a specific compound or material coated onto the target surface. Besides for using water contact angles for determining hydrophilicity/hydrophobicity and contact angles of n-hexadecane for deciding oleophilicity/oleophobicity, the contact angle of oleic acid on the modified glass surface is utilized as a practical measure for evaluating the anti-fingerprint property of the surface modified by the specific compound.

Figure 1:
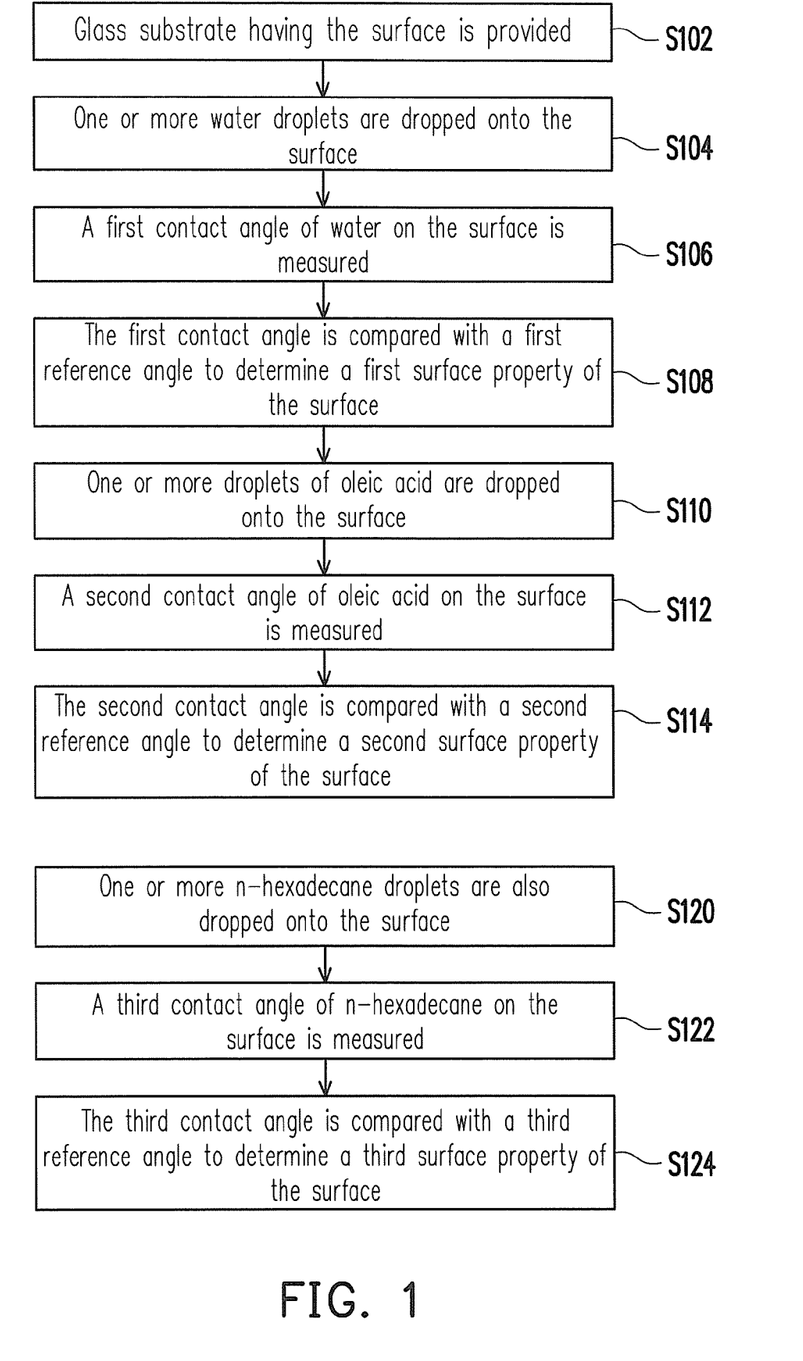
FIG. 1 is a flow chart showing the process steps of the method for evaluating one or more surface properties of a surface according to embodiments of the present invention.

FIG. 1 is a flow chart showing the process steps of the method for evaluating one or more surface properties of a surface according to embodiments of the present invention.

In the present application, a method for evaluating one or more surface properties of a surface of a glass substrate is provided. At first, the glass substrate having the surface is provided (Step 102). One or more water droplets are dropped onto the surface (Step 104). A first contact angle of water on the surface of the glass substrate is measured (Step 106), and then the first contact angle is compared with a first reference angle to determine a first surface property of the surface (Step 108). Also, one or more droplets of oleic acid are dropped onto the surface (Step 110). A second contact angle of oleic acid on the surface of the glass substrate is measured (Step 112) and the second contact angle is compared with a second reference angle to determine a second surface property of the surface (Step 114).

Optionally, one or more n-hexadecane droplets are also dropped onto the surface (Step 120). A third contact angle of n-hexadecane on the surface of the glass substrate is measured (Step 122) and the third contact angle is compared with a third reference angle to determine a third surface property of the surface (Step 124).

According to embodiments of the present invention, the first surface property is a hydrophilic/hydrophobic property and the first reference angle may be 40 degrees. The second surface property is an anti-fingerprint property and the second reference angle may be 40 degrees. The third surface property is an oleophilic/oleophobic property, and the third reference angle may be 40 degrees.

In addition, by using the aforementioned approach, the anti-fingerprint compound(s) or material(s) suitable for modifying or coating the surface of the glass substrate may be further evaluated, so as to determine the best compound or material for anti-fingerprint or stain-proof purposes.

For example, an organooxysilane compound may be used to modify the surface of the glass substrate before providing the glass substrate, and the modified surface is evaluated using the aforementioned method to determine the first and second surface properties of the modified surface.

In the following contexts, different types of organooxysilane compounds are used to modify the glass surface as the experimental samples. These modified glass surfaces (target surfaces) are studied to demonstrate that the contact angle of oleic acid is an effective measure to evaluate the anti-finger property of these surfaces modified by different organooxysilane compounds.

Organooxysilanes are silicone-based compounds, which can react with inorganic substrates such as glass to form stable covalent (siloxane, Si—O—Si) bonds and provide functionality (e.g. amine, phenyl, alkyl, fluoro groups and etc.) on the substrates. Such functionalization can alter the properties of the surface of the substrate (substrate surface). Generally, organooxysilanes tend to form self-assembled monolayers (SAMs) on the surfaces. Organooxysilane SAMs with appropriate organic functionalities (i.e. functional groups) may be applied to the substrate surface so that the surface exhibits the amphiphobic property.

In this embodiment, by using the sol-gel method, organooxysilane SAMs with various kinds of organic functional groups are applied to the glass surface and the amphiphobic property of the glass surface is investigated. In the present invention, a straightforward approach is provided to investigate the amphiphobic property of the surface. The hydrophobic and oleophobic properties of organosiloxane modified surface are determined by measuring contact angles of droplets of water and n-hexadecane on the surface. The contact angle of droplets of oleic acid is also measured to evaluate the anti-fingerprint property on the modified glass surfaces, since oleic acid is an amphiphilic unsaturated fatty acid and is a main component of human-fingerprint. Moreover, the surface morphology or roughness of the modified glasses is investigated by an atomic force microscopy (AFM). The anti-fingerprint property is assessed in connection with the amphiphobic property and roughness of these ultrathin organic films.

Experiments

Modification of Glass Surface by Organooxysilane SAMs

Figure 2:
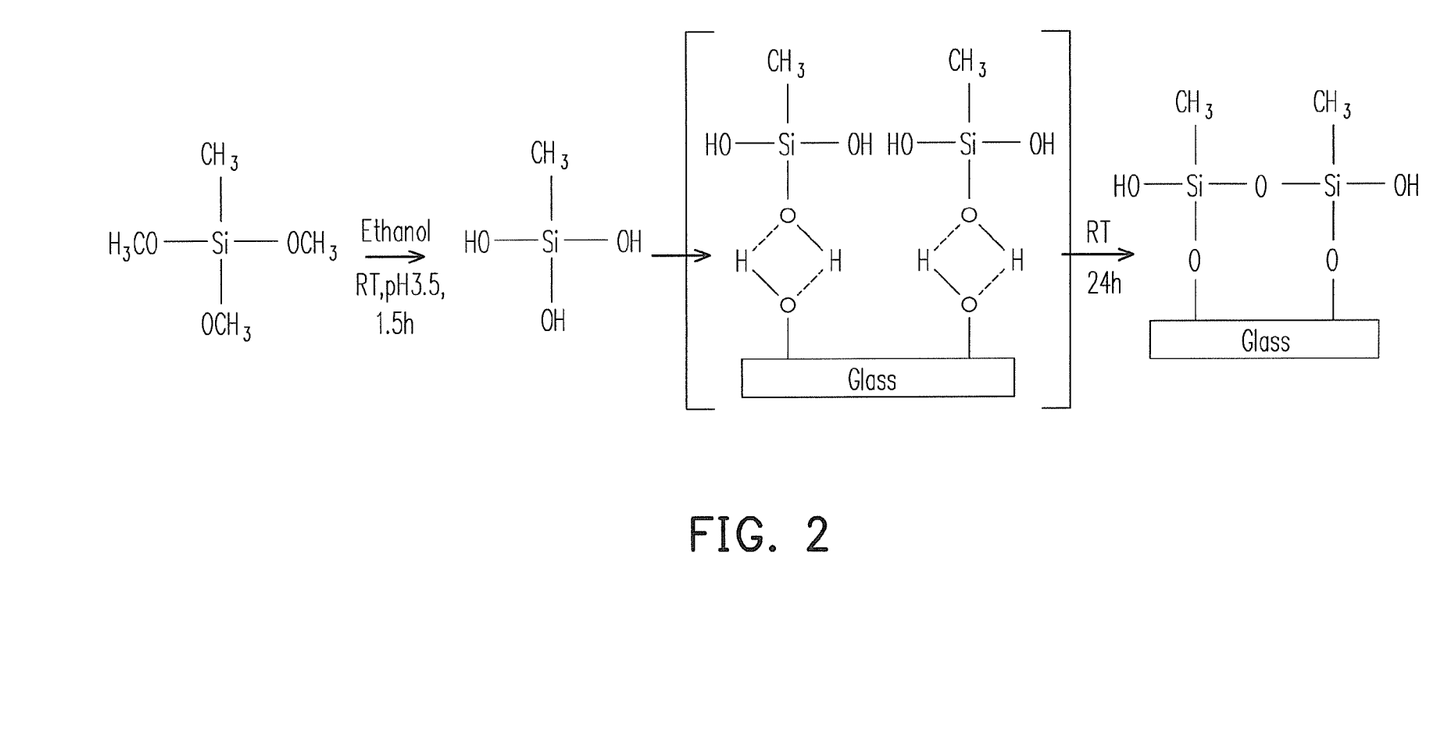
FIG. 2 is the reaction scheme of organooxysilanes SAMs modified glass.

Organooxysilanes SAMs modified glass is prepared based on the possible reaction scheme as shown in the FIG. 2.

At first, a glass substrate is immersed in a piranha solution ($H_2SO_4$: $H_2O_2$=3:1) for 30 min for cleaning and hydroxyl groups are introduced on the glass surface. Then, the glass substrate is rinsed with water several times. An aqueous solution of organooxysilane (2% v/v) is prepared by mixing organooxysilane with water, ethanol (10% v/v) and 0.1 M HCl (3.3% v/v) and the pH of the aqueous solution is adjusted to 3.5 to hydrolyze organooxysilane for 1.5 h at the room temperature. Then, the clean glass substrate is dipped into the aqueous solution of hydrolyzed organooxysilane and reacted with the solution under stirring for 24 hours at the room temperature. The obtained organooxysilane SAMs modified (organooxysilane SAMs coated) glass substrate is washed with ethanol to remove the unreacted chemicals and dried overnight in the oven at 110° C.

In general, the glass surface is modified in an acidic organic-aqueous solvent environment at a pH value of 3.5. The acidic organic-aqueous solvent environment includes an organic solvent (5-30% v/v), a source of free hydride ion (1-5% v/v), and water (95-70% v/v), relative to the total volume of the mixture solution.

By applying organooxysilane SAMs with various kinds of organic functional groups to the glass surface, different samples of modified glass substrates are prepared. For example, organooxysilanes with hydrophilic moieties, such as 3-aminopropyltriethoxysilane (APTES) and 3-glycidoxypropyl trimethoxysilane (GPS) or organooxysilanes with hydrophobic moieties, such as trimethoxymethylsilane (TMS), isobutyl(trimethoxy)silane (ITMS), tetraethyl orthosilicate (TEOS) and octadecyltrimethoxysilane (ODS) are used to modify the glass substrate and the properties of the obtained samples are measured. In addition, organooxysilanes with phenyl moieties, such as trimethoxyphenylsilane (TMPS) and trimethoxy(2-phenylethyl)silane (TMPES) or organooxysilanes with fluorinated moieties, such as trimethoxy (3,3,3-trifluoropropyl)silane (TMFS) and 1H,1H, 2H,2H-perfluorodecyltriethoxysilane (PFDES) are applied to prepare the modified glass surface and the properties of the obtained samples are measured. The polycondensation of silanol groups of the hydrolyzed alkoxy (e.g. methoxy and ethoxy) moieties with hydroxyl groups on the glass surface results in stable siloxane (Si—O—Si) bonds and provides organic moieties on the glass surface. The chemicals and reagents used in the experiments are described as follows. TMS, PFDES, TMPES, TMFS, TMPS, ITMS, and oleic acid are purchased from Aldrich Chemical Co. TEOS (98%), APTES (99%), 3-glycidoxypropyl trimethoxysilane (GPS) and n-hexadecane are purchased from AcrosOrganics Ltd. Octadecyltrimethoxysilane (ODS) is purchased from WakoChemicals Co.

-continued

Trimethoxyphenylsilane (TMPS)

Trimethoxy(2-phenylethyl)silane (TMPES)

Trimethoxy (3,3,3-trifluoropropyl) silane (TMFS)

1H,1H,2H,2H-Perfluorodecyl triethoxysilane (PFDES)

Measurements

The contact angles of water, n-hexadecane and oleic acid on the modified glass substrate are measured by means of a conventional digital camera. An aliquot (10 µL) of test liquid is dropped on the modified glass surface, and the contact angle is measured at a few seconds after dropping. AFM observation is performed using a Digital Instruments Nano-Scope III apparatus.

Figure 3:
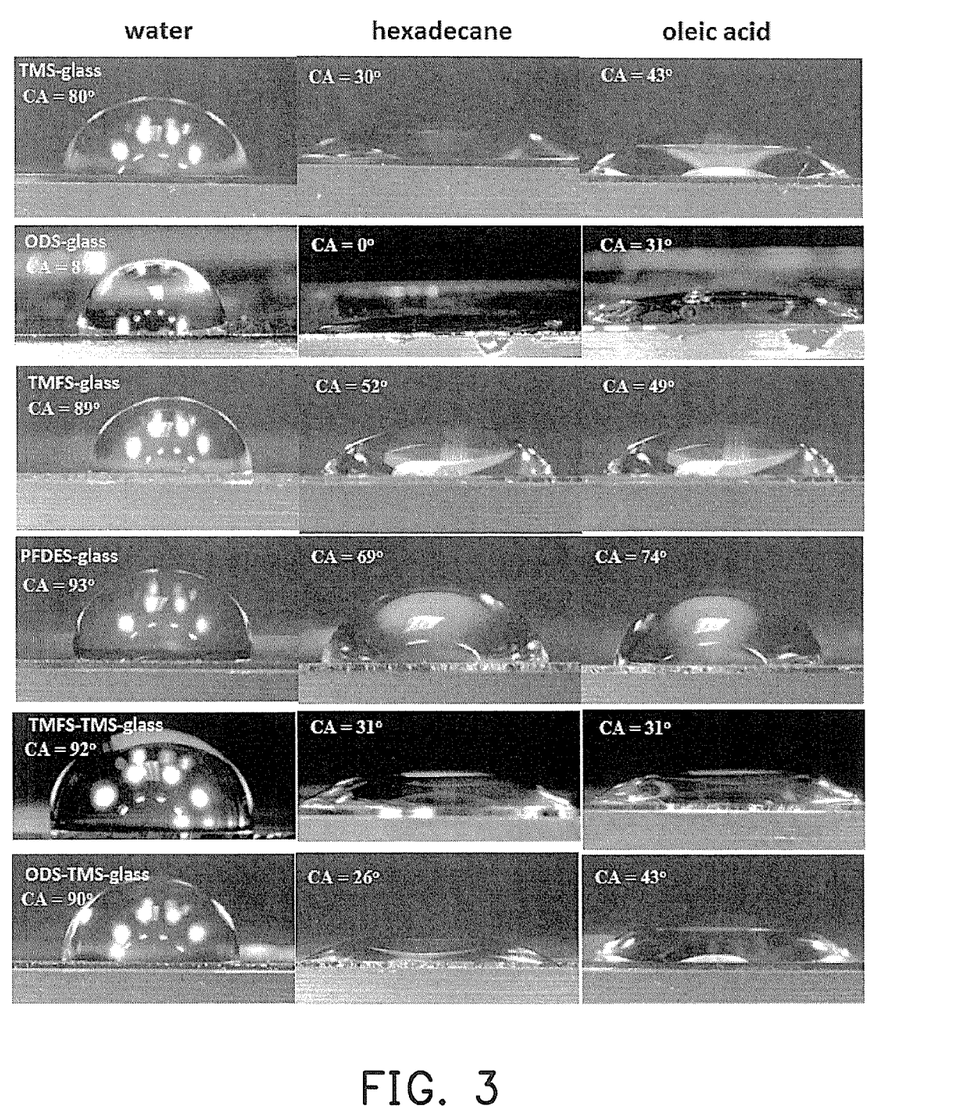
FIG. 3 shows the contact angles of water, hexadecane and oleic acid on TMS-, ODS-, TMFS-, PFDES-, TMFS/TMS- and ODS/TMS-glass surfaces according to embodiments of the present invention.

FIG. 3 shows the contact angles of water, hexadecane and oleic acid on TMS-, ODS-, TMFS-, PFDES-, TMFS/TMS- and ODS/TMS-glass surfaces according to embodiments of the present invention. The contact angles of water, n-hexadecane and oleic acid on the modified glass surfaces of various glass samples are compared with those on the bare glass surface, as shown in FIG. 3 and the obtained contact angles are listed in Table 1, in order to evaluate the property changes of the surfaces after surface modification. Also, the surface tension and roughness of the surfaces of these glass samples are listed in Table 1.

TABLE 1

| Substrate | Critical surface tension (mN/m) | Contact angle | | | Roughness (nm) |
|---|---|---|---|---|---|
| | | Water | n-hexadecane | Oleic acid | |
| Bare glass | 47.0 | 37° | 14° | 18° | 1-2 |
| APTES-glass | 35.0 | 80° | 0° | 26° | 1-2 |
| GPS-glass | 42.5 | 80° | 0° | 31° | 2-10 |
| TEOS-glass | 23.5 | 74° | 15° | 26° | 2-17 |
| TMS-glass | 22.5 | 78° | 30° | 41° | 2-10 |
| ITMS-glass | 20.9 | 92 | 18° | 35° | 1-5 |
| ODS-glass | 27.6 | 87° | 0° | 31° | 1-4 |
| TMPS-glass | 40.0 | 90° | 14° | 25° | 2-30 |
| TMPES-glass | 28.0 | 90° | 16° | 27° | 2-20 |
| TMFS-glass | 33.5 | 93° | 51° | 48° | 1-2 |
| PFDES-glass | 18.1 | 93° | 69° | 74° | 1-20 |
| APTES/TMS-glass | — | 90° | 0° | 21° | 1-2 |
| TMFS/TMS-glass | — | 92° | 31° | 31° | 1-2 |
| ODS/TEOS-glass | — | 68° | 15° | 26° | 2-15 |
| ODS/TMS-glass | — | 90° | 26° | 43° | 2-10 |

The formation of organosiloxane SAMs on the glass surfaces is confirmed by the water contact angles. The hydrophilic property may be classified as water contact angles below 40° and the hydrophobic character is indicated by water contact angles larger than 40°. The water contact angle of the bare glass surface is 37°, which indicates moderate hydrophilicity. In the meantime, after organosiloxane SAMs are coated onto the glass surface, the water contact angle increases remarkably to 74°-93° (as summarized in Table 1), depending on the organic moiety of siloxanes. The results indicate that the modified surfaces become hydrophobic in the order of hydrophilic moiety<phenyl moiety≤fluorinated moiety. In addition, the hydrophobicity of the glass surfaces modified with siloxane with hydrophobic moiety slightly varies depending on the organic moieties used, Generally, the differences between the water contact angles of the glass surfaces modified with siloxane with hydrophobic moiety is not significant (74°-92°).

For evaluation of the oleophobic property, n-hexadecane is used as a test liquid. The contact angles of n-hexadecane (hexadecane contact angles) on the organooxysilane-modified glass surfaces are summarized in Table 1. The contact angle of n-hexadecane on the bare glass is 14°, which indicates the moderate oleophobicity. The oleophilicity of organosiloxane SAMs-modified surfaces may be associated with the hydrophobic property of SAMs. It is observed that APTES- and GPS-treated glass surfaces exhibit high oleophilicity (the contact angles of n-hexadecane being 0°) as well as a hydrophobic ODS-treated glass surface (the contact angles of n-hexadecane being 0°). The results that these modified surfaces are well wetted by n-hexadecane agree with the results of water contact angles in the same category of glass surfaces treated with organosilanes with hydrophobic moieties. Even though APTES- and GPS-treated glass surfaces have hydrophilic moieties, amine terminals of APTES close to the hydrophilic glass surface possibly form hydrogen bonding with hydroxyl groups so that the hydrophobic propyl groups are exposed on the modified glass surface. Similarly, for GPS-treated glass surfaces, the hydrophobic alkyl groups are exposed on glass surface. The observed results of hexadecane contact angles reveals that the oleophobicity of phenyl-SAM glass is almost the same as that of bare glass and fluorinated-SAM glass is rather oleophobic. The order of oleophobicity of the glass surfaces modified with siloxane with various moieties is hydrophilic moiety<phenyl moiety<fluorinated moiety, the same as that of hydrophobicity determined from water contact angles. This suggests the increase of amphiphobicity in this order. The oil-repellency of SAMs with hydrophobic moiety depends on their chemical structure, independent to the variation of the hydrophobicity determined from water contact angles. While TEOS- and ITMS-treated glass surfaces posses the moderate oleophobicity, TMS-treated surface is rather oleophobic.

Liquids with a surface tension below the critical surface tension of a substrate can wet the substrate surface. The critical surface tension ($\gamma_c$) of organosiloxane SAMs are listed in Table 1. As the surface tension of n-hexadecane ($\gamma_c$=27.6 mN/m) is lower than the critical surface tensions ($\gamma_c$=35-42.5 mN/m) of SAMs with hydrophilic moiety, hexadecane spreads easy on the modified glass surfaces. On the other hand, because the surface tension of hexadecane is higher than those of TMS- and TMPES-glass surfaces, hexadecane cannot easily spread on such surfaces.

The glass substrates with fluorinated moiety (TMFS- and PFDES-glass surfaces) exhibit significantly high contact angles of hexadecane of 51° and 69°, respectively. Fluorinated-glass surfaces may possess very low surface energy due to the existence of —CF$_3$ and —CF$_2$ groups, which leads to high hexadecane contact angles and water contact angles and implies amphiphobic behavior. The obtained results reveal that the PFDES-glass surface shows higher oleophobic property than TMFS-glass due to the existence of several CF$_2$ groups, with a critical surface tension of 18 mN/m. It should be noted that high oleophobicity (or amphiphobicity) of the fluorinated surfaces is caused not only by the polarity of the C—F bond and the weak molecular interaction of fluorinated compounds but also by the close-packing of functional CF$_3$ terminals.

As the major ingredient of human fingerprint is oleic acid (40.6%) and/or its derivatives, oleic acid can be used as a substitutive for fingerprint. The contact angle of oleic acid on the modified glass substrates may be different from contact angles of water and/or hexadecane, because oleic acid is an amphiphilic unsaturated fatty acid with a hydrophobic oleyl moiety and a hydrophilic carboxylic acid moiety.

In the present application, oleic acid is used as a test liquid to verify the anti-fingerprint property of the modified glass surfaces. The surface tension of pure oleic acid is 31.8 mN/m, which is in a category comparable to the surface tension of human fingerprints of 20-50 mN/m and comparable to the surface tension of organosilane-modified glass surfaces (20.9-42.5 mN/m in Table 1), except for PFDES-treated glass (18 mN/m).

As shown in Table 1, the contact angle of oleic acid on the bare glass is lowest (18°). For the modified glass surfaces with hydrophilic and phenyl moieties, the contact angles of oleic acid thereon are moderate (25°-31°). For the modified glass surfaces with fluorinated moieties, the contact angles of oleic acid thereon are highest (48° and 74°). The modified glass surfaces with hydrophobic moieties exhibit different contact angles (26°-41°), depending on the organic moieties thereon. The tendency (order) of anti-fingerprint property is almost consistent with the order of oleophobicity determined from hexadecane contact angles. However, the contact angles of oleic acid on the modified glass surfaces are larger than those of hexadecane, since oleic acid has a surface tension higher than hexadecane. As expected, the contact angle of oleic acid on PFDES-glass is highest, and second highest on TMFS-glass. It is noted that the contact angle of oleic acid on TMS-glass is only slightly lower than that on TMFS-glass. Considering the surface tension of TMS-glass is only 22.5 mN/m (Table 1), the TMS surface can be considered to be as amphiphobic as the fluorinated surfaces as the TMS-glass surface resists wetting by the hydrocarbon oils.

Two types of organooxysilanes are used in combination as the hybrid SAMs coated to the glass surfaces to study their effects on the amphiphobic properties of the SAMs-coated glass surfaces. The hybrid SAMs with the hydrophilic-hydrophobic moiety (APTES/TMS), hydrophobic-hydrophobic moiety (ODS/TEOS and ODS/TMS) and fluorinated-hydrophobic moiety (TMFS/TMS) are coated on the glass surface by the sol-gel method. The obtained contact angles are listed in Table 1. The results reveal that the synergistic effects are shown in increasing the water contact angles for the hybrids of hydrophobic (TMS) moiety with the hydrophilic (APTES) and hydrophobic (ODS) moieties. That is, the water contact angles on APTES/TMS-glass surface and ODS/TMS-glass surface (both 90°) are obviously higher than those on the glass surfaces individually coated with the respective moiety. TMFS/TMS-glass has a water contact angle similar to TMFS-glass, rather than TMS-glass, which indicates the dominant contribution of TMFS. However, hexadecane contact angles seem to be predominated by the modified compounds as followings: APTES>TMS, TEOS>ODS, TMS>ODS, TMS>TMFS. Concerning the contact angles of oleic acid, it is noticed that the anti-fingerprint effects of TMFS and TMS decrease after hybridization. Meanwhile, TMS is dominant in hybrid with ODS and the anti-fingerprint effect of ODS/TMS-glass is same as or superior to TMS-glass. On the other hand, APTES is dominant in controlling such surface property in the case of APTES/TMS-glass.

Figure 4:
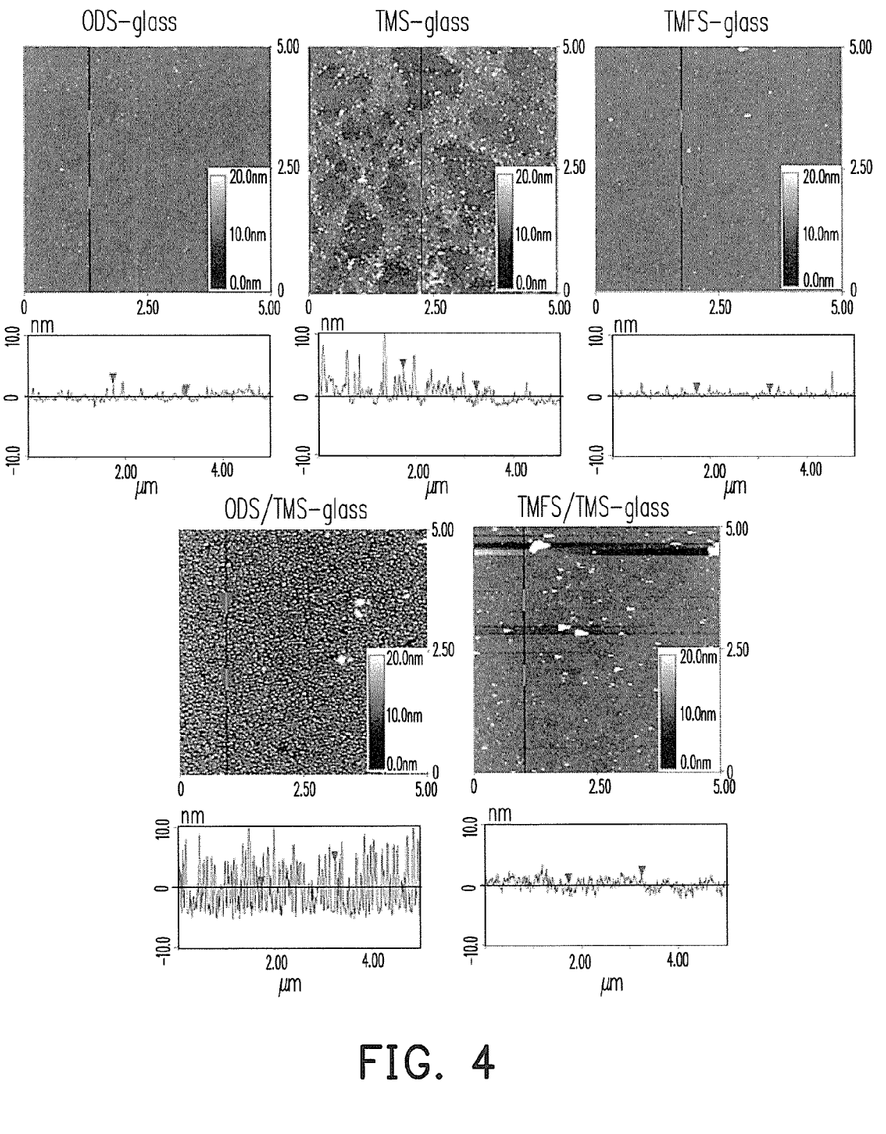
FIG. 4 shows an atomic force microscopy images of ODS-, TMS-, TMFS-, ODS/TMS-, and TMFS/TMS-glass surfaces.

The surface roughness may also causes changes in the amphiphobic property. FIG. 4 shows an atomic force microscopy (AFM) images of ODS-, TMS-, TMFS-, ODS/TMS-, and TMFS/TMS-glass surfaces. As shown in FIG. 4, AFM images of ODS-, TMS-, TMFS-, ODS/TMS-, and TMFS/TMS-glass surfaces are observed to evaluate the morphology of the modified glass surfaces. The observed roughness of the modified glass surfaces is listed in Table 1 as well. The surfaces of APTES-, ITMS-, ODS- and TMFS-glass having a roughness below 5 nm are smoother than those of other surfaces with a roughness up to 30 nm. For the hybrid SAMs-coated glass surfaces, the surface morphology is dominated by one of components, that is, by APTES, TMFS, TEOS, and TMS for APTES/TMS-, TMFS/TMS-, ODS/TEOS- and ODS/TMS-glasses, respectively. This phenomenon is consistent with the dominant role of the respective component on contact angles of oleic acid, as discussed above.

On the other hand, the AFM images of ODS/TMS-glass and TMS-glass display protrusions with a height below 10 nm on the glass surfaces. Unexpectedly, ODS/TMS-glass and TMS-glass exhibit high contact angles of oleic acid thereon, which are comparable to TMFS-glass. It is suggested that these two modified glass surfaces (treated by non-fluorinated TMS or its hybrid with ODS) provide "bumpy structures" in the nanometer scale on the glass surfaces, which enhances the repellency of oleic acid or the amphiphobic character.

From the above experiments, instead of considering the environmental-unfriendly fluorinated organooxysilane compounds, trimethoxymethylsilane (TMS) or a hybrid of trimethoxymethylsilane (TMS) and octadecyltrimethoxysilane (ODS) are suitable organooxysilane compounds for anti-fingerprint purposes.

The examples listed herein are merely for illustrations and not to limit the scope of the present invention.

As the anti-fingerprint property is not necessarily consistent with hydrophobicity and/or oleophobicity and thus the evaluation of the anti-fingerprint property using merely water or organic solvents may be inaccurate. Using the additional test liquid, oleic acid, the contact angles of oleic acid may be used to fortify the evaluation of the anti-fingerprint property of a target surface.

To sum up, instead of using water contact angles for determining hydrophilicity/hydrophobicity and contact angles of n-hexadecane for deciding oleophilicity/oleophobicity, the contact angle of oleic acid on the modified glass surface is utilized as a practical measure for evaluating the anti-fingerprint property of the target surface. By doing so, the surface characteristics of the target surface(s) can be determined more precisely and accurately.

While the invention has been described and illustrated with reference to specific embodiments thereof, these descriptions and illustrations do not limit the invention. It should be understood by those skilled in the art that various changes may be made and equivalents may be substituted without departing from the true spirit and scope of the invention as defined by the appended claims. The illustrations may not be necessarily being drawn to scale. There may be distinctions between the artistic renditions in the present disclosure and the actual apparatus due to manufacturing processes and tolerances. There may be other embodiments of the present invention which are not specifically illustrated. The specification and the drawings are to be regarded as illustrative rather than restrictive. Modifications may be made to adapt a particular situation, material, composition of matter, method, or process to the objective, spirit and scope of the invention. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A coating material for modifying a glass surface to provide an anti-fingerprint property, comprising at least a self-assembling monolayer formed on the glass surface by using an organooxysilane compound as a precursor, wherein the glass surface is modified in an acidic organic-aqueous solvent environment.

2. The coating material as claimed in claim 1, wherein the organooxysilane compound is trimethoxymethylsilane (TMS).

3. The coating material as claimed in claim 1, wherein the organooxysilane compound is a hybrid of trimethoxymethylsilane (TMS) and octadecyltrimethoxysilane (ODS).

4. The coating material as claimed in claim 1, wherein the acidic organic-aqueous solvent environment includes organic solvent (5-30% v/v), a source of free hydride ion (1-5% v/v), and water (95-70% v/v).

5. The coating material as claimed in claim 4, wherein the organic-aqueous solvent environment is at a pH value of 3.5.

6. A method for evaluating one or more surface properties of a surface of a glass substrate, comprising:

providing the glass substrate having the surface;
providing one or more water droplets to the surface;
measuring a first contact angle of water on the surface of the glass substrate;
comparing the first contact angle with a first reference angle to determine a first surface property of the surface;
providing one or more droplets of oleic acid on the surface;
measuring a second contact angle of oleic acid on the surface of the glass substrate; and
comparing the second contact angle with a second reference angle to determine a second surface property of the surface.

7. The method as claimed in claim 6, further comprising:
providing one or more n-hexadecane droplets to the surface;
measuring a third contact angle of n-hexadecane on the surface of the glass substrate; and
comparing the third contact angle with a third reference angle to determine a third surface property of the surface.

8. The method as claimed in claim 6, further comprising modifying the surface of the glass substrate with an organooxysilane compound before providing the glass substrate, so that the surface of the modified glass substrate becomes a modified surface and the first and second surface properties of the modified surface are determined.

9. The method as claimed in claim 8, further comprising:
providing one or more n-hexadecane droplets to the modified surface;
measuring a third contact angle of n-hexadecane on the modified surface; and
comparing the third contact angle with a third reference angle to determine a third surface property of the modified surface.

* * * * *